United States Patent
Kamimura et al.

(10) Patent No.: US 8,575,190 B2
(45) Date of Patent: Nov. 5, 2013

(54) METHOD OF PREVENTING OR AMELIORATING PSORIASIS USING PYRROLOQUINOLINE QUINONE COMPOUNDS

(75) Inventors: Ayako Kamimura, Ibaraki (JP);
Toshikazu Kamiya, Ibaraki (JP);
Masahiko Nakano, Niigata (JP);
Kazutoshi Kikkawa, Chiba (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 1 day.

(21) Appl. No.: 12/742,351

(22) PCT Filed: Nov. 12, 2008

(86) PCT No.: PCT/JP2008/070578
§ 371 (c)(1),
(2), (4) Date: May 11, 2010

(87) PCT Pub. No.: WO2009/063897
PCT Pub. Date: May 22, 2009

(65) Prior Publication Data
US 2010/0261749 A1    Oct. 14, 2010

(30) Foreign Application Priority Data
Nov. 14, 2007 (JP) ................................. 2007-296022

(51) Int. Cl.
*A61K 31/44* (2006.01)
(52) U.S. Cl.
USPC .......................................... 514/292; 514/863
(58) Field of Classification Search
None
See application file for complete search history.

(56) References Cited

U.S. PATENT DOCUMENTS

| 5,369,112 A | 11/1994 | Maeda et al. |
| 6,790,855 B2 * | 9/2004 | Pasternak et al. ............. 514/282 |
| 2002/0004484 A1 | 1/2002 | Pasternak et al. |
| 2003/0105031 A1 * | 6/2003 | Rosenbloom .................. 514/27 |

FOREIGN PATENT DOCUMENTS

| JP | 02-268118 | 11/1990 |
| JP | 03-112912 | 5/1991 |
| JP | 5-78247 | 3/1993 |
| JP | 08-020512 | 1/1996 |
| JP | 08-020585 | 1/1996 |
| JP | 2004-512260 | 4/2004 |

OTHER PUBLICATIONS

Miyachi, "Oxidative stress in skin diseases", Shukan Igaku no Ayumi (2006) 330-33 (Partial Translation).
Miyachi, "Free radicals in dermatology", Pharma Medica, vol. 8, No. 4 (1990) 67-71 (Partial Translation).
Naito, et al., "Effects of Pyrroloquinoline Quinone (PQQ) and PQQ-Oxazole on DNA Synthesis of Cultured Human Fibroblasts", Life Sciences, vol. 52, No. 24 (1993) 1909-15.
Nakai, "Psoriasis vulgaris: NO generation resulting from iNOS expression in skin lesions", Hifu Rinsho, vol. 49, No. 7 (2007) 767-75.
Bergboer et al., Pathogenesis of Atopic Dermatitis and Psoriasis: Focus on the Epidermal Differentiation Complex, Open Derm. J., vol. 4 (2010) 48-51.
Guttman-Yassky et al., Psoriasis and atopic dermatitis: The same, only different, J. Allergy Clin. Immunol., vol. 127 (2011) 1420-32.
Makiura et al., Atopic Dermatitis-like Symptoms in HR-1 Hairless Mice Fed a Diet Low in Magnesium and Zinc, J. Int. Med. Res., vol. 32 (2004) 392-99.

* cited by examiner

*Primary Examiner* — Sreeni Padmanabhan
*Assistant Examiner* — Jody Karol
(74) *Attorney, Agent, or Firm* — Fitzpatrick, Cella, Harper & Scinto

(57) ABSTRACT

The present invention provides a method for preventing or ameliorating skin psoriasis by applying as an active ingredient, a compound represented by general formula (I) or a salt thereof:

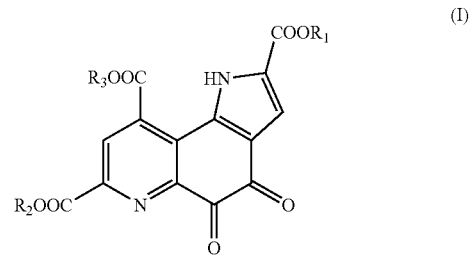

(wherein $R_1$, $R_2$, and $R_3$ simultaneously or separately represent a lower alkyl, lower alkenyl, lower alkynyl, aralkyl, araryl, or phenyl group, or a hydrogen atom).

5 Claims, No Drawings

METHOD OF PREVENTING OR AMELIORATING PSORIASIS USING PYRROLOQUINOLINE QUINONE COMPOUNDS

TECHNICAL FIELD

The present invention relates to a preventing or ameliorating agent for skin psoriasis containing, as an active ingredient, pyrroloquinoline quinone, an ester thereof, or a salt of either thereof.

BACKGROUND ART

The skin has barrier functions that allow it to serve as a protective organ to maintain vital activity. In addition, the skin surface may be smooth, dried, wrinkled, etc. Therefore, it can be said that the skin is an organ that plays a cosmetic role. In order to exhibit barrier functions, it is important for the skin to retain moisture mainly with intercellular lipids and natural moisturizing factors in the horny layer. It is known that there is a correlation between the moisture content in the horny layer and skin surface conditions such as smoothness and dryness (see Non-Patent Document 1).

Examples of methods that have been conducted as a means for retaining or improving skin moisture-retaining properties include a method wherein horny layer barrier functions are compensated with the use of a plugging agent such as vaseline ointment or a water-in-oil emulsifying drug formulation; a method wherein the horny layer moisture content is increased with the use of a moisturizing agent such as sorbitol or glycerine; a method wherein skin inflammation is alleviated with the use of an anti-inflammatory drug such as glycyrrhizinic acid; and a method wherein skin cells are activated by vitamins, hormones, and the like (see Non-Patent Document 2).

Psoriasis is chronic inflammatory keratosis with formation of scales. The disease is characterized by excessive growth/abnormal differentiation of epidermal cells, angiogenesis, and invasion of activated T cells (CD3-positive cells) into the epidermis/dermis, etc. For treatment of psoriasis, a variety of anti-inflammatory drugs described above are used and moisturizing agents and the like are used in combination. However, the use of such agents is merely symptomatic treatment. Therefore, there are no radical therapies known to the public.

Pyrroloquinoline quinone (hereinafter referred to as "PQQ") was discovered as a coenzyme of methanol dehydrogenase contained in a methanol-assimilating bacterium in 1979, (see Non-Patent Documents 3 and 4). PQQ has been detected not only from microorganisms but also from edible plants such as soybeans, broad beans, green pepper, potatoes, parsley, and spinach, and processed food products such as vinegar, tea, cocoa, natto, and tofu (see Non-Patent Document 5). In addition, it has been reported that PQQ is present in humans and rats (see Non-Patent Document 6). Therefore, it is a highly safe substance.

PQQ has been known to have effects such as cell growth promoting effects (see Patent Document 1), effects of removing active oxygen (see Patent Document 2), melanin production inhibitory and skin whitening effects (see Patent Document 3), ultraviolet absorbing effects (see Patent Document 4), and antiallergic effects (see Patent Document 5).

However, it has been unknown that PQQ, an ester thereof, or a salt of either thereof has preventing or ameliorating effects for skin psoriasis.

Non-Patent Document 1: "Archives of Dermatology," 1985, vol. 121, pp. 642-645

Non-Patent Document 2: "Fragrance Journal" 1999, vol. 10, p. 29

Non-Patent Document 3: "Nature," 1979, vol. 230, pp. 843-844

Non-Patent Document 4: "FEBS Letters," 1979, vol. 108, pp. 443-446

Non-Patent Document 5: "Biochemical Journal," 1995, vol. 307, pp. 331-333

Non-Patent Document 6: "Biochimica et Biophysica Acta," 1992, vol. 1156, pp. 62-66

Patent Document 1: JP Patent Publication (Kokai) No. 61-58584 A (1986)

Patent Document 2: JP Patent Publication (Kokai) No. 5-078247 A (1993)

Patent Document 3: JP Patent Publication (Kokai) No. 8-020512 A (1996)

Patent Document 4: JP Patent No. 3625493

Patent Document 5: JP Patent Publication (Kokai) No. 63-174931 A (1988)

DISCLOSURE OF THE INVENTION

Problem to be Solved by the Invention

It is an object of the present invention to provide a preventing or ameliorating agent for skin psoriasis.

Means for Solving Problem

The present invention provides a preventing or ameliorating agent for skin psoriasis described in (1) below. In addition, the present invention provides a method for preventing or ameliorating psoriasis described in (2) below and a method for using such agent described in (3) below.

(1) A preventing or ameliorating agent for skin psoriasis, containing, as an active ingredient, a compound [hereinafter referred to as compound (I)] represented by general formula (I) or a salt thereof:

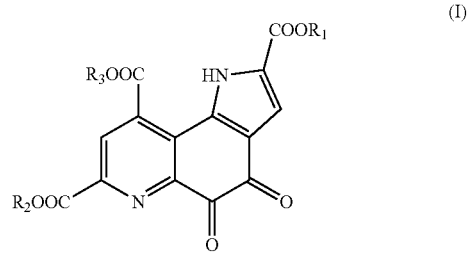

(wherein $R_1$, $R_2$, and $R_3$, simultaneously or separately represent a lower alkyl, lower alkenyl, lower alkynyl, aralkyl, araryl, or phenyl group, or a hydrogen atom).

(2) A method for preventing or ameliorating skin psoriasis, comprising administering a compound represented by general formula (I) or a salt thereof in a therapeutically effective dose to a patient:

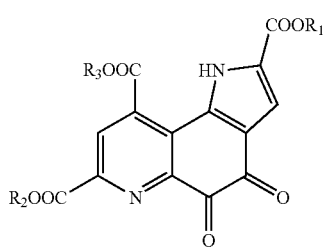

(I)

(wherein $R_1$, $R_2$, and $R_3$, simultaneously or separately represent a lower alkyl, lower alkenyl, lower alkynyl, aralkyl, araryl, or phenyl group, or a hydrogen atom).

(3) Use of a compound represented by general formula (I) for the production of a preventing or ameliorating agent for skin psoriasis or a salt thereof:

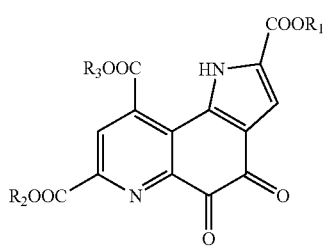

(I)

(wherein $R_1$, $R_2$, and $R_3$, simultaneously or separately represent a lower alkyl, lower alkenyl, lower alkynyl, aralkyl, araryl, or phenyl group, or a hydrogen atom).

Effects of the Invention

The present invention provides a preventing or ameliorating agent for skin psoriasis.

This description includes part or all of the contents as disclosed in the description and/or drawings of Japanese Patent Application No. 2007-296022, which is a priority document of the present application.

BEST MODE FOR CARRYING OUT THE INVENTION

In the definition of compound (I), $R_1$, $R_2$, and $R_3$, simultaneously or separately represent a lower alkyl, lower alkenyl, lower alkynyl, aralkyl, araryl (alkylaryl), or phenyl group, or a hydrogen atom. An alkyl portion of such lower alkyl, aralkyl, or araryl is, for example, linear or branched alkyl with a carbon number of 1 to 6. Specific examples thereof include methyl, ethyl, propyl, isopropyl, butyl, sec-butyl, tert-butyl, pentyl, isopentyl, neopentyl, and hexyl. Methyl or ethyl is particularly preferable.

An example of lower alkenyl is linear or branched alkenyl with a carbon number of 2 to 6. Specific examples thereof include vinyl, allyl, 1-propenyl methacryl, crotyl, 1-butenyl, 3-butenyl, 2-pentenyl, 4-pentenyl, 2-hexenyl, and 5-hexenyl.

An example of lower alkynyl is linear or branched alkynyl with a carbon number of 2 to 6. Specific examples thereof include ethynyl, propynyl, butynyl, pentynyl, and hexynyl.

An example of aralkyl is aralkyl with a carbon number of 7 to 15. Specific examples thereof include benzyl, phenethyl, benzhydryl, and naphthylmethyl.

An example of an aryl portion of araryl is aryl with a carbon number of 6 to 14. Specific examples thereof include phenyl, naphthyl, and anthryl. Therefore, examples of araryl include methylphenyl and ethylphenyl.

PQQ, which is the above compound represented by general formula (I) wherein each of $R_1$, $R_2$, and $R_3$ represents a hydrogen atom, can be produced by an organic chemical method (e.g., J. Am. Chem. Soc., 103, 5599-5600, (1981)) and a fermentation method such as a method for producing pyrroloquinoline quinone by culturing bacteria having methanol-assimilating ability and the ability to produce pyrroloquinoline quinone in a culture solution which contains methanol as a carbon source and in which an iron compound concentration is controlled (JP Patent Publication (Kokai) No. 1-218597 A (1989)).

PQQ ester represented by compound (I) can be synthesized from PQQ according to a general esterification reaction.

For example, PQQ triester can be readily synthesized by a method wherein PQQ or a salt thereof is allowed to react with alcohols under acidic conditions (e.g., JP Patent Publication (Kokai) No. 3-123781 A (1991) or JP Patent Publication (Kokai) No. 3-145492 A (1991)), a method wherein PQQ or a salt thereof is allowed to react with alkyl halide, alkenyl halide, alkynyl halide, aralkyl halide, araryl halide, or the like under the presence of bases, or the like. In addition, a monoester or a diester can be obtained by partially hydrolyzing PQQ triester obtained by the above method under acidic or basic conditions.

The thus obtained compound (I) can be separated/purified from a reaction solution by a general method such as column chromatography, a recrystallization method, or a solvent extraction method. In addition, a various means such as elemental analysis, NMR spectrum or IR spectrum analysis, and mass spectrometry are used for identification of the compound (I).

Examples of a salt of compound (I) include: alkali metal salts such as sodium salts and potassium salts; alkaline-earth metal salts such as magnesium salts and calcium salts; organic amine salts such as ammonium, triethanolamine, and triethylamine; and basic amino acid salts such as lysine and arginine.

The agent of the present invention can prevent or ameliorate psoriasis characterized by epidermal thickening and T cell invasion.

A compound (I) or a salt thereof can be directly administered as the preventing or ameliorating agent for skin psoriasis of the present invention. However, it is desirable to provide the agent in the form of a variety of drug formulations.

Such drug formulation contains, as an active ingredient, the compound (I) or a salt thereof. In addition, it may further contain a different arbitrary active ingredient for treatment purposes. Further, the drug formulation can be produced by an arbitrary method that has been well known in the art of drug formulation by mixing the active ingredient with at least one type of pharmacologically acceptable carrier.

It is desirable that the most effective administration route of drug formulation would be selected for treatment. Examples thereof include oral administration and parenteral administration such as intravenous, intraperitoneal, or subcutaneous administration. However, oral administration is preferable.

Examples of dosage forms that can be used for administration include: oral agents such as tablets, powders, granules, pills, suspensions, emulsions, infusions and decoctions, capsules, syrups, liquid, elixirs, extracts, tinctures, and fluid extracts; and parenteral agents such as parenteral injections, intravenous fluids, creams, and suppositories. The agent in the form of an oral agent is preferably used.

When the agent of the present invention is formulated into an oral agent, it can be used with an additive such as an excipient, a binder, a disintegrator, a lubricant, a dispersant, a suspension, an emulsifier, a diluent, a buffer, an antioxidant, or a microbial inhibitor.

In the case involving the use of liquid preparations such as syrup appropriate for oral administration, the preparations can be formulated by addition of water; sugars such as sucrose, sorbitol, and fructose; glycols such as polyethylene glycol and propylene glycol; oils such as sesame oil, olive oil, and soybean oil; antiseptics such as p-hydroxy benzoate esters; parahydroxy benzoate derivatives such as methyl parahydroxy benzoate; preservatives such as sodium benzoate; and flavors such as strawberry flavor and peppermint flavor.

In addition, in the case involving the use of tablets, powders, and granules that are appropriate for oral administration, the preparations can be formulated by addition of: sugar such as lactose, glucose, sucrose, mannitol, and sorbitol; starch from potatoes, wheat, and corn; an inorganic substance such as calcium carbonate, calcium sulfate, sodium bicarbonate, and sodium chloride; an excipient of a plant-derived powder such as crystalline cellulose, a sweetroot powder and gentian powder; a disintegrator such as starch, agar, gelatin powder, crystalline cellulose, carmellose sodium, carmellose calcium, calcium carbonate, sodium bicarbonate, and sodium alginate; a lubricant such as magnesium stearate, talc, hydrogenated plant oil, macrogol, and silicone oil; a binder such as polyvinyl alcohol, hydroxypropyl cellulose, methyl cellulose, ethyl cellulose, carmellose, gelatin, and starch paste liquid; a surfactant such as fatty acid ester; and a plasticizer such as glycerine.

It is also possible to add an additive generally used for foods and beverages to the drug formulation appropriate for oral administration. Examples of additives include sweeteners, colorants, preservatives, thickening stabilizers, antioxidants, coloring agents, bleaches, antifungal agents, gum bases, bittering agents, enzymes, gloss agents, acidulants, seasonings, emulsifiers, fortifiers, production agents, aroma chemicals, and spice extracts.

The drug formulation appropriate for oral administration may be directly used in the form of, for example, a powder food product, a sheet-type food product, a bottled food product, a canned food product, a retort food product, a capsule food product, a tablet food product, a liquid food product, or a drink. In addition, the drug formulation may be used in the form of food or beverage such as health food, functional food, nutritional supplement, or food for specified health use for prevention and amelioration of skin psoriasis.

For example, a parenteral injection appropriate for parenteral administration comprises preferably a sterilized aqueous agent which contains a compound (I) or a salt thereof and which is isotonic to the blood of a recipient. For example, for a parenteral injection, an injectable solution is prepared with the use of a carrier comprising a salt solution, a glucose solution, or a mixture of a salt solution and a glucose solution.

In addition, it is also possible to add at least one supplemental component to a parenteral agent, wherein such component is selected from the group consisting of diluents, antiseptics, flavors, excipients, disintegrators, lubricants, binders, surfactants, and plasticizers, which are described above for an oral agent.

The concentration of a compound (I) or a salt thereof in the preventing or ameliorating agent for skin psoriasis of the present invention is adequately determined depending on the type of drug formulation, effects expected to be obtained as a result of administration of the drug formulation, and the like. For instance, in the case of an oral agent, the concentration of a compound (I) or a salt thereof is generally 0.1 to 100% by weight, preferably 0.5 to 70% by weight, and particularly preferably 1 to 50% by weight.

The dosage and the number of doses of the preventing or ameliorating agent for skin psoriasis of the present invention would vary depending on dosage form, patients' ages and body weights, characteristics of symptoms to be treated, and severity of a symptom. However, for administration, the dosage in terms of a compound (I) or a salt thereof for an adult per day is generally 0.5 mg to 10000 mg, preferably 0.5 mg to 5000 mg, and more preferably 5 mg to 1000 mg once daily or separately over several times a day.

The dosing period is not particularly limited. However, it is generally 1 day to 1 year and preferably 2 weeks to 3 months.

In addition, the drug formulation of the present invention can be used not only for humans but also for animals except for humans (hereinafter referred to as "nonhuman animals"). Examples of nonhuman animals include mammals, birds, reptiles, amphibians, and fish. Preferably, the drug formulation can be used for nonhuman animals belonging to the Mammalia class.

When the preventing or ameliorating agent for skin psoriasis of the present invention is administered to a nonhuman animal, the dosage and the number of doses would vary depending on dosage form, and animal age and type. However, the agent is administered in the form of the compound (I) or a salt thereof in a dose of generally 0.01 mg to 200 mg, preferably 0.1 mg to 100 mg, and more preferably 0.1 mg to 20 mg per 1 kg of body weight once daily or separately over several times a day. The dosing period is not particularly limited. However, in general, it is 1 day to 1 year and preferably 2 weeks to 3 months.

EXAMPLES

Hereinafter, a Test Example in which preventing or ameliorating effects for skin psoriasis of the compound (I) were examined is described below.

Test Example

For testing, HOS: HR-1 mice (female, 4 weeks old, purchased from Hoshino Laboratory Animmals, Inc.) were used. Mice were raised under conditions of a room temperature of 22±3° C. and a humidity of 50±25% while being fed with feed and water ad libitum.

Each test group consisted of 8 mice. The mice of the $1^{st}$ group were fed with a commercially available powder feed product "CE-2." The mice of the $2^{nd}$ group were fed with a specialty feed product (produced by Nosan Corporation). The mice of the $3^{rd}$ group were fed with a specialty feed product containing 0.0089% by weight of pyrroloquinoline quinone disodium salt (hereinafter referred to as PQQ disodium salt, produced by Mitsubishi Gas Chemical Company, Inc.). In addition, it has been known that HOS: HR-1, mice develop dry skin after being fed with the above specialty feed product (The Journal of international medical research pharmacology, 32, 392-399 (2004)).

Upon the initiation of feeding with each feed product and 2, 4, and 6 weeks later, the transepidermal water loss (TEWL) of the right buttock of each mouse was determined with the use of a Tewameter TM210 (Courage+Khazaka electronic GmbH, Germany) and the average value for each group was calculated. Table 1 shows results of the determination of the transepidermal water loss value (TEWL value) from week 0 to week 6 after the initiation of the test for each group.

As is apparent from table 1, in the $2^{nd}$ group which had developed dry skin, the transepidermal water loss value (TEWL value) significantly increased compared with that of the $1^{st}$ group. Meanwhile, in the $3^{rd}$ group to which PQQ disodium salt had been added, the transepidermal water loss value (TEWL value) was suppressed to a level lower than that in the $2^{nd}$ group to which PQQ disodium salt had not been added.

TABLE 1

| | TEWL value (g/cm²/hour) Feeding period (weeks) | | | |
|---|---|---|---|---|
| | 0 | 2 | 4 | 6 |
| $1^{st}$ group | 4.95 | 7.13 | 8.06 | 7.46 |
| $2^{nd}$ group | 4.95 | 21.23 | 28.48 | 32.13 |
| $3^{rd}$ group | 4.94 | 17.85 | 27.00 | 29.93 |

In addition, the skin moisture content (conductance) was determined with SKICON-200 (produced by IBS) and the average value for each group was calculated. Table 2 lists results of determination of the skin moisture content from week 0 to week 6 after the initiation of the test.

As is apparent from table 2, in the $2^{nd}$ group, which developed dry skin, the skin moisture content (conductance) significantly decreased compared with that of the $1^{st}$ group. Meanwhile, in the $3^{rd}$ group, to which PQQ disodium salt had been added, the skin moisture content (conductance) increased to a greater extent than that in the $2^{nd}$ group, to which PQQ disodium salt had not been added.

The above results show that PQQ disodium salt caused a decrease in the transepidermal water loss value (TEWL value) and an increase in the skin moisture content (conductance) in the test with the use of dry skin mouse models. Therefore, it has been revealed that PQQ disodium salt prevents skin dryness and thus exhibits preventing or ameliorating effects for psoriasis.

TABLE 2

| | Conductance (μS) Feeding period (weeks) | | | |
|---|---|---|---|---|
| | 0 | 2 | 4 | 6 |
| $1^{st}$ group | 439.03 | 230.43 | 176.05 | 232.80 |
| $2^{nd}$ group | 453.00 | 56.65 | 35.48 | 29.23 |
| $3^{rd}$ group | 414.55 | 67.83 | 41.95 | 39.03 |

Paraffin sections of mouse dorsal skin fixed with neutral buffer containing 10 vol % formalin were prepared for the determination of epidermis thickness. Table 3 lists results of the determination of epidermis thickness 6, weeks after the initiation of the test.

As is apparent from table 3, in the $2^{nd}$ group, which developed dry skin, epidermis thickness significantly increased compared with that of the $1^{st}$ group. Meanwhile, in the $3^{rd}$ group, to which PQQ disodium salt had been added, epidermis thickening was suppressed.

TABLE 3

| | Test group | | |
|---|---|---|---|
| | 1 | 2 | 3 |
| Thickness (μm) | 19.25 | 71.88 | 64.03 |
| Standard deviation | 2.00 | 10.41 | 11.35 |

The number of mast cells in dermis was determined with the use of May-Grunwald-Giemsa staining specimens. The counting area was the dermis located above the cutaneous muscle. The number of cells in the dermis (per 1 mm of the baseline) was obtained by dividing the determined cell number by the length of a straight line extending between both ends of the cutaneous muscle (baseline). For a significant difference test, a test for equality of variance was carried out based on the Bartlett method. In the case of the equal variance ($p>0.05$), one-way analysis of variance and a Tukey's test were conducted. In the case of the unequal variance ($p\leq0.05$), a Kruskal-Wallis test and a Steel-Dwass test were conducted. Table 4 shows results of the determination of the number of mast cells in dermis per basal line (1 mm) 6 weeks after the initiation of the test.

As is apparent from table 4, in the $2^{nd}$ group, which had developed dry skin, the number of mast cells in the dermis significantly increased compared with that of the $1^{st}$ group. Meanwhile, in the $3^{rd}$ group, to which PQQ disodium salt had been added, the number of mast cells in the dermis was suppressed.

TABLE 4

| | Test group | | |
|---|---|---|---|
| | 1 | 2 | 3 |
| Number of cells/mm basal line | 39.98 | 70.33 | 54.62* |
| Standard deviation | 11.89 | 9.09 | 8.37 |

*$p < 0.05$ for the $2^{nd}$ group

In addition, counting of the number of CD3-positive T lymphocytes in the epidermis was carried out with the use of anti-CD3 immunostained specimens. The counting area was the dermis located above the cutaneous muscle. The number of cells in the epidermis (per mm of the baseline) was obtained by dividing the determined cell number by the length of a straight line extending between both ends of the cutaneous muscle (baseline). For a significant difference test, a test for equality of variance was carried out based on the Bartlett method. In the case of the equal variance ($p>0.05$), one-way analysis of variance and a Tukey's test were conducted. In the case of the unequal variance ($p\leq0.05$), a Kruskal-Wallis test and a Steel-Dwass test were conducted. Table 5 shows results of the determination of the number of CD3-positive cells in epidermis per basal line (1 mm) 6 weeks after the initiation of the test.

As is apparent from table 5, in the $2^{nd}$ group, which had developed dry skin, the number of CD3-positive cells in the epidermis significantly increased compared with that of the $1^{st}$ group. Meanwhile, in the $3^{rd}$ group, to which PQQ disodium salt had been added, the number of CD3-positive cells in the epidermis was suppressed.

The above results showed that PQQ disodium salt has effects of inhibiting epidermal thickening and invasion of mast cells and CD-3 positive cells characteristically observed in psoriasis cases.

TABLE 5

| | Text group | | |
|---|---|---|---|
| | 1 | 2 | 3 |
| Number of cells/mm basal line | 9.48 | 36.16 | 18.95* |
| Standard deviation | 2.99 | 13.52 | 6.12 |

*$p < 0.05$ for the $2^{nd}$ group

Next, the present invention is hereafter described in detail with reference to the following examples showing formulation examples of the preventing or ameliorating agent for skin psoriasis of the present invention, although the technical scope of the present invention is not limited thereto.

Example 1

Water is added to the composition with the formulation listed in table 6 to result in a volume of 1000 mL such that a drink for prevention and amelioration of skin psoriasis (10 bottles) is produced.

TABLE 6

| Composition | Content |
|---|---|
| PQQ disodium salt | 100 mg |
| Vitamin C | 1 g |
| Vitamin B1 | 5 mg |
| Vitamin B2 | 10 mg |
| Vitamin B6 | 25 mg |
| Liquid sugar | 150 g |
| Citric acid | 3 g |
| Flavor | 1 g |

Example 2

Tablets for prevention and amelioration of skin psoriasis (155 mg per tablet) are produced by a general method with the formulation listed in table 7.

TABLE 7

| Composition | Content |
|---|---|
| PQQ disodium salt | 5 mg |
| Lactose | 90 mg |
| Cornstarch | 30 mg |
| Synthetic aluminum silicate | 12 mg |
| Carboxymethylcellulose calcium | 15 mg |
| Magnesium stearate | 3 mg |

Example 3

A preventing or ameliorating agent for skin psoriasis (505 mg per pack) is produced by a general method with the formulation listed in table 8.

TABLE 8

| Composition | Content |
|---|---|
| PQQ diethyl ester | 5 mg |
| Lactose | 300 mg |
| Cornstarch | 200 mg |

Example 4

Hard capsules for prevention and amelioration of skin psoriasis (115 mg per capsule) are produced with the formulation listed in table 9.

TABLE 9

| Composition | Content |
|---|---|
| PQQ monoallyl ester | 5 mg |
| Lactose | 60 mg |
| Cornstarch | 30 mg |
| Hydroxypropyl cellulose | 20 mg |

Lactose (60 mg) and cornstarch (30 mg) are added to PQQ monoallyl ester (5 mg), followed by mixing. An aqueous solution containing hydroxypropyl cellulose (20 mg) is added thereto, followed by kneading. Then, granules are produced with the use of an extrusion granulator by a general method. Hard capsules are prepared by filling gelatin hard capsules with the granules.

Example 5

Soft capsules for prevention and amelioration of skin psoriasis (125 mg per capsule) are produced with the formulation listed in table 10.

TABLE 10

| Composition | Content |
|---|---|
| PQQ disodium salt | 5 mg |
| Soybean oil | 120 mg |

PQQ disodium salt (5 mg) is added to soybean oil (120 mg), followed by mixing. Then, soft capsules are filled with the resultant with the use of a rotary die automatic forming machine by a general method. Thus, soft capsules are produced.

All publications, patents, and patent applications cited herein are incorporated herein by reference in their entirety.

The invention claimed is:

1. A method for ameliorating dermatological symptoms of psoriasis, comprising administering 0.5 to 10,000 mg of a compound represented by formula (I) or a salt thereof to a patient in need thereof:

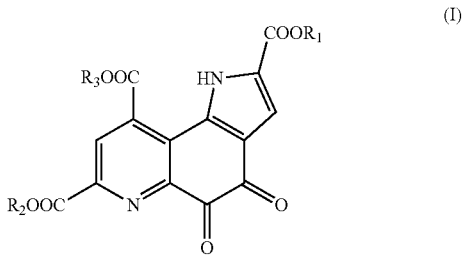

wherein $R_1$, $R_2$, and $R_3$ independently represent a lower alkyl, lower alkenyl, lower alkynyl, aralkyl, araryl, or phenyl group, or a hydrogen atom, with the proviso at least one of $R_1$, $R_2$, and $R_3$ represents a hydrogen atom, and the compound of formula (I) or the salt thereof is the only active compound administered to said patient.

2. A method for ameliorating dermatological symptoms of psoriasis, comprising administering 0.5 to 10,000 mg of a compound represented by formula (I) or a salt thereof to a patient in need thereof:

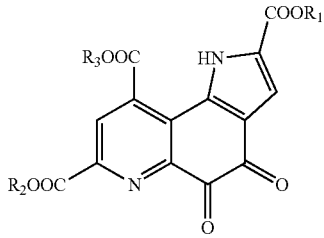

wherein $R_1$, $R_2$, and $R_3$ independently represent a lower alkyl, lower alkenyl, lower alkynyl, aralkyl, araryl or phenyl group, and the compound of formula (I) or the salt thereof is the only active compound administered to said patient.

3. A method for ameliorating dermatological symptoms of psoriasis, comprising administering 0.5 to 10,000 mg of a compound represented by formula (I) to a patient in need thereof:

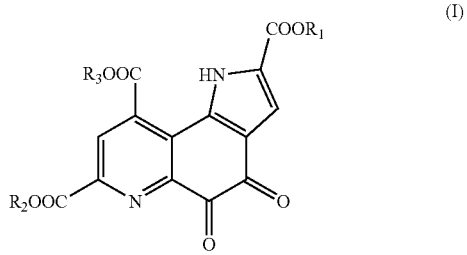

wherein $R_1$, $R_2$, and $R_3$ each represent a hydrogen atom, and the compound of formula (I) is the only active compound administered to said patient.

4. The method according to any one of claim 1, 2 or 3 wherein 0.5 to 5,000 mg of the compound represented by formula (I) or a salt thereof is administered to said patient.

5. The method according to claim 4, wherein 0.5 to 1,000 mg of the compound represented by formula (I) or a salt thereof is administered to said patient.

* * * * *